United States Patent
Vallana

(10) Patent No.: US 11,819,422 B2
(45) Date of Patent: Nov. 21, 2023

(54) INTERSOMATIC CAGE FOR VERTEBRAL STABILIZATION

(71) Applicant: SPS S.r.l., Scarmagno (IT)

(72) Inventor: Valerio Vallana, Turin (IT)

(73) Assignee: S.P.S. S.r.l., Scarmagno (IT)

(*) Notice: Subject to any disclaimer, the term of this patent is extended or adjusted under 35 U.S.C. 154(b) by 0 days.

(21) Appl. No.: 17/349,985

(22) Filed: Jun. 17, 2021

(65) Prior Publication Data

US 2021/0393418 A1    Dec. 23, 2021

(30) Foreign Application Priority Data

Jun. 18, 2020   (IT) .................. 102020000014587

(51) Int. Cl.
  *A61F 2/44*   (2006.01)
  *A61F 2/30*   (2006.01)

(52) U.S. Cl.
  CPC .......... *A61F 2/447* (2013.01); *A61F 2/30771* (2013.01); *A61F 2/442* (2013.01); *A61F 2002/3082* (2013.01); *A61F 2002/30677* (2013.01); *A61F 2002/30772* (2013.01)

(58) Field of Classification Search
  CPC ......... A61F 2/442; A61F 2/4455; A61F 2/447
  See application file for complete search history.

(56) References Cited

U.S. PATENT DOCUMENTS

| | | | |
|---|---|---|---|
| 9,132,021 B2* | 9/2015 | Mermuys ................ | A61F 2/447 |
| 10,022,245 B2* | 7/2018 | Frasier ................... | A61F 2/442 |
| 10,478,313 B1* | 11/2019 | Sweeney, III ......... | A61F 2/4611 |
| 10,682,238 B2* | 6/2020 | Petersheim ........... | A61F 2/4611 |
| 11,058,551 B2* | 7/2021 | Abbasi .................... | A61L 27/06 |
| 11,147,682 B2* | 10/2021 | Trudeau ............... | A61F 2/30965 |
| 2004/0258732 A1 | 12/2004 | Shikinami | |
| 2007/0016163 A1 | 1/2007 | Santini et al. | |
| 2010/0114317 A1* | 5/2010 | Lambrecht ............. | A61F 2/442 623/17.11 |
| 2010/0228296 A1* | 9/2010 | Vraney ................... | A61F 2/447 606/279 |
| 2010/0262244 A1* | 10/2010 | Savage-Erickson .... | A61F 2/442 623/17.16 |
| 2011/0282392 A1* | 11/2011 | Murphy ............. | A61K 38/1875 606/279 |
| 2012/0179261 A1* | 7/2012 | Soo ...................... | A61F 2/4455 623/17.16 |

(Continued)

FOREIGN PATENT DOCUMENTS

| | | |
|---|---|---|
| EP | 3459502 A1 | 3/2019 |
| WO | 0143620 A2 | 6/2001 |
| WO | 2012010327 A1 | 1/2012 |

OTHER PUBLICATIONS

"grating" Dictionary.com. Accessed Oct. 5, 2022 https://www.dictionary.com/browse/grating (Year: 2022).*
Italian Search Report dated Feb. 25, 2021. 9 pages.

*Primary Examiner* — Eduardo C Robert
*Assistant Examiner* — Steven J Cotroneo
(74) *Attorney, Agent, or Firm* — RMCK Law Group PLC

(57) ABSTRACT

Intersomatic cage for vertebral stabilization, including a generally prismatic body consisting of surface receptacles containing slow prolonged release substances selected from the classes of anti-inflammatory, anti-infection and bone regrowth promoter drugs. The receptacles are in the form of gratings of grooves.

3 Claims, 2 Drawing Sheets

(56) References Cited

U.S. PATENT DOCUMENTS

| | | | |
|---|---|---|---|
| 2012/0303127 A1* | 11/2012 | Ullrich, Jr. | A61F 2/3094 |
| | | | 623/17.16 |
| 2014/0172103 A1* | 6/2014 | O'Neil | A61F 2/4611 |
| | | | 623/17.16 |
| 2014/0303733 A1* | 10/2014 | Davis | A61F 2/4455 |
| | | | 623/17.16 |
| 2015/0148907 A1* | 5/2015 | Kleiner | A61F 2/4455 |
| | | | 606/94 |
| 2015/0265414 A1* | 9/2015 | Mermuys | A61F 2/447 |
| | | | 623/17.16 |
| 2016/0022431 A1* | 1/2016 | Wickham | A61F 2/447 |
| | | | 623/17.16 |
| 2016/0199193 A1* | 7/2016 | Willis | A61F 2/447 |
| | | | 623/17.16 |
| 2016/0213486 A1* | 7/2016 | Nunley | A61F 2/447 |
| 2017/0056179 A1* | 3/2017 | Lorio | A61F 2/447 |
| 2017/0239066 A1* | 8/2017 | Walsh | A61F 2/447 |
| 2018/0303624 A1* | 10/2018 | Shoshtaev | A61F 2/4611 |
| 2019/0298542 A1* | 10/2019 | Kloss | A61F 2/3094 |

* cited by examiner

INTERSOMATIC CAGE FOR VERTEBRAL STABILIZATION

CROSS-REFERENCE TO RELATED APPLICATION

This application claims priority to Italian Patent Application No. 102020000014587 filed Jun. 18, 2020. The disclosure of the above application is incorporated herein by reference in its entirety.

FIELD OF THE INVENTION

The present invention relates to an intersomatic cage for vertebral stabilization designed to be inserted between two contiguous vertebrae so as to space them apart and thus keep them at a mutual distance such to restore the intervertebral space, creating the decompression of the nerve roots and the acceleration of the intersomatic fusion.

STATE OF THE PRIOR ART

Intersomatic cages thus made comprise a generally prismatic-shaped body provided with a nose protruding from the front end of the body and designed to be inserted between two contiguous vertebrae during the surgical insertion of the intersomatic cage.

Distinctive examples of intersomatic cages for vertebral stabilization are described and illustrated, for example, in Italian patent applications no. 102019000023913 and no. 102020000001210 on behalf of the Applicant in question, not published at the filing or priority date of the present application.

These cages are applied using invasive surgical techniques which typically provide for—following insertion of the nose between the two vertebrae—rotations alternately in the direction of the cage and in the opposite direction, performed by means of a suitable manual instrument, while it is pushed so as to be wedged between the vertebrae.

Following the application, the intervertebral region is normally subject to inflammations and also to infections in some cases. Bone regrowth may also be insufficient and unsuitable to effectively incorporate the cage over time.

Documents WO2012/010327A1 and US2011/282392A1 disclose intersomatic cages of the type defined above are known provided with receptacles containing slow release medical substances.

SUMMARY OF THE INVENTION

The object of the present invention is to solve the aforementioned problems and in particular to provide an intersomatic cage which allows to limit if not even eliminate the negative clinical consequences for patients following the application thereof.

According to the invention, this object is achieved essentially due to the fact that said surface receptacles containing slow prolonged release substances selected from the classes of anti-inflammatory, anti-infection and bone regrowth promoter drugs consist of gratings of grooves formed both at least on the side walls of the body and on the nose.

Preferably the body is hollow and said surface receptacles are provided for on the inner and outer surfaces of said side walls of the body.

BRIEF DESCRIPTION OF THE DRAWINGS

The invention will now be described in detail with reference to the attached drawings, provided purely by way of non-limiting example, wherein.

DETAILED DESCRIPTION OF THE INVENTION

Figure 1:
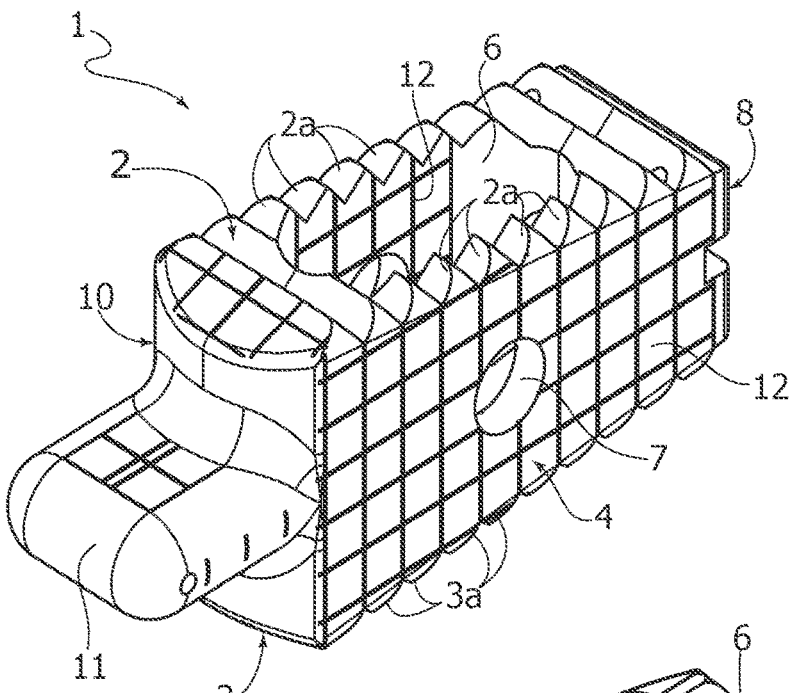
FIG. 1 is a front perspective view of the intersomatic cage according to the invention.
Figure 2:
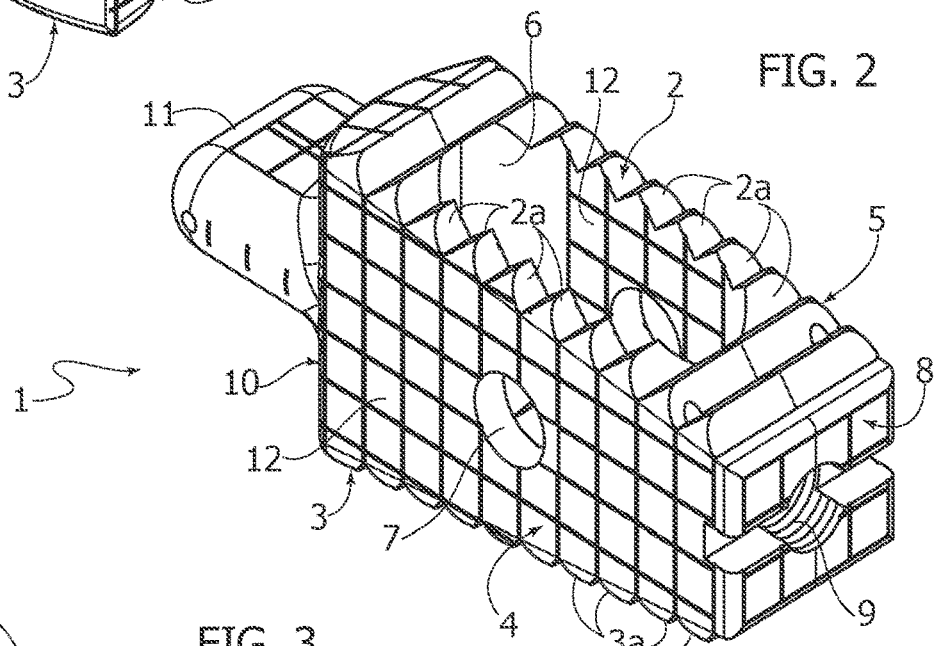
FIG. 2 is a dorsal perspective view of the cage.
Figure 3:
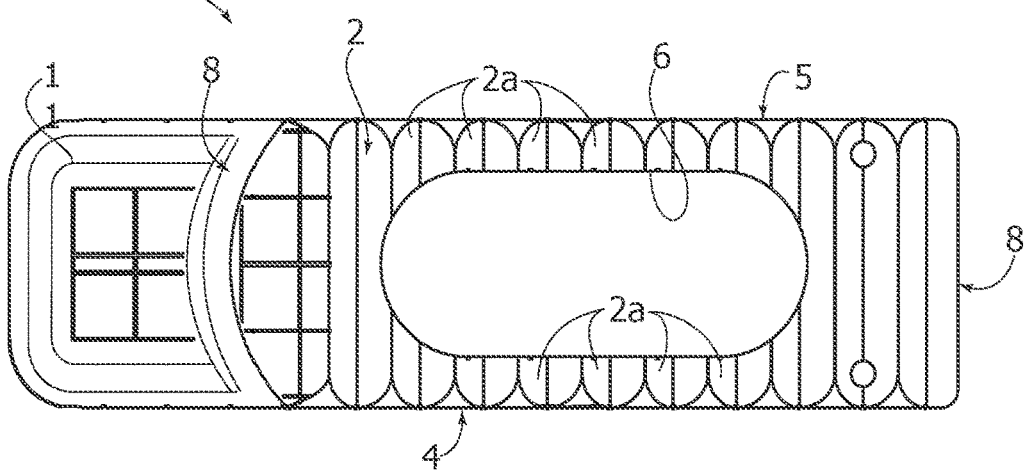
FIG. 3 is a top plan view of the cage.

With reference to the figures, the intersomatic cage according to the invention consists of a generally prismatic-shaped and more precisely parallelepiped-shaped monolithic body 1, having an upper face 2 and a lower face 3 (with reference to the implanted position of the cage in the intervertebral space of a subject with an upright spine), and side faces 4, 5.

The upper and lower faces 2, 3 are both preferably formed with respective anchoring formations consisting of parallel indentations 2a, 3a.

The body 1 is hollow, thanks to the fact that a through opening in the form of a slot 6 passes vertically through it between the upper 2 and lower 3 faces. Furthermore, circular holes 7 pass through the side walls 4, 5 of the body 1.

Figure 4:
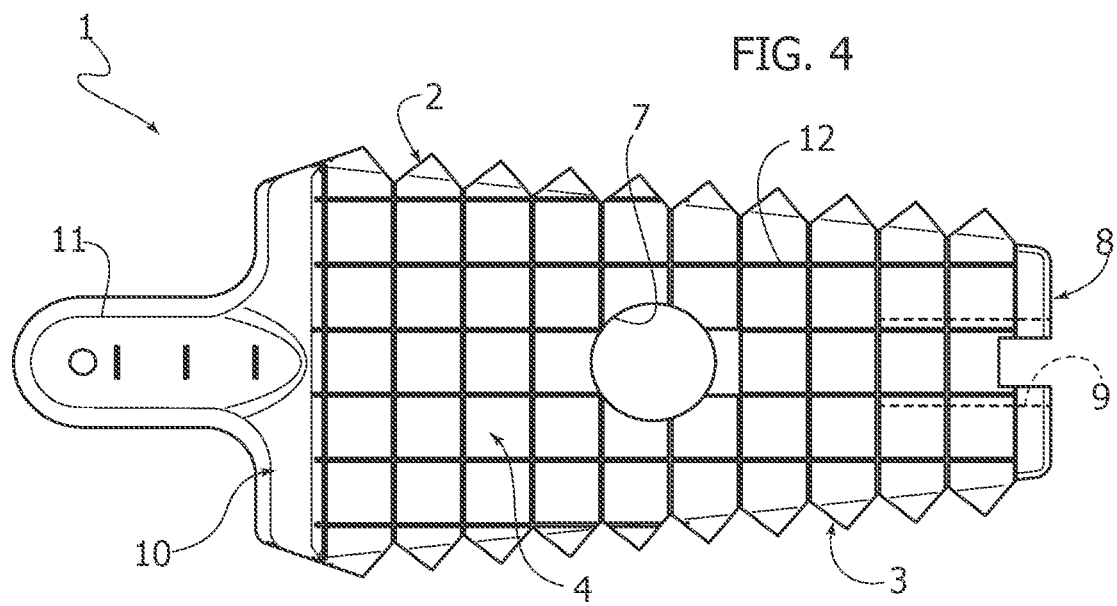
FIG. 4 is a side elevational view of the cage.
Figure 5:
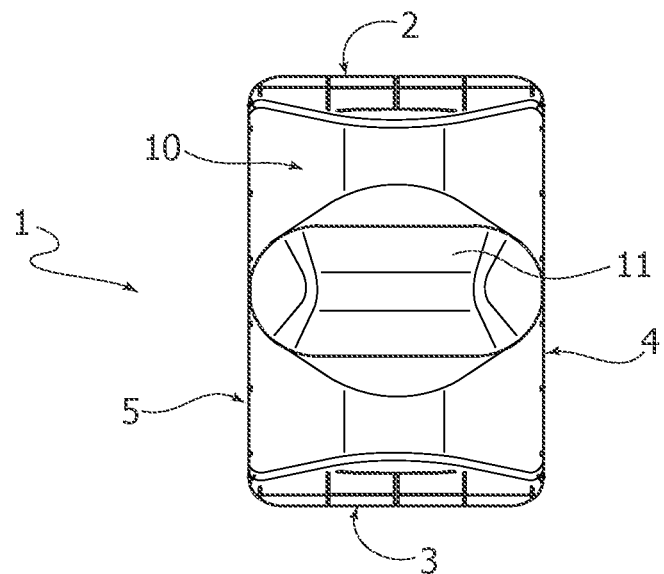
FIG. 5 is a front elevational view of FIG. 4.
Figure 6:
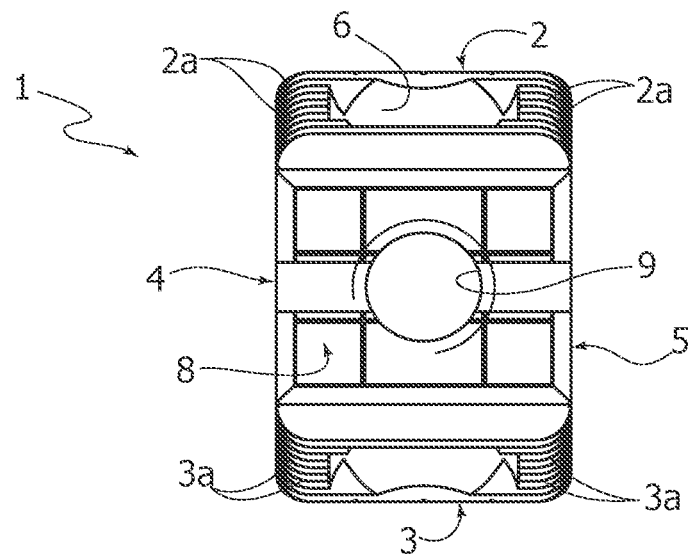
FIG. 6 is a dorsal elevational view of FIG. 4.

As observable in FIG. 4, the body 1 has a height, measured between the upper 2 and lower 3 faces, which decreases slightly toward the rear end thereof, indicated with 8 and in which a recess 9 for the introduction of a tool for the surgical insertion of the cage into the intervertebral space. This instrument, not illustrated, is configured so as to engage axially and torsionally with the recess 9 so as to be able to rotate the body 1 alternately in a clockwise and anti-clockwise direction or vice versa while being simultaneously pushed.

A nose 11—which has the function of paving the way by dilating the intervertebral space during the process for inserting the intersomatic cage—protrudes from the front end of the body 1, indicated with reference numeral 10.

The shape of the nose 11 is conveniently similar to that described and illustrated in the previously cited Italian patent application n° 102019000023913 on behalf of the Applicant in question, not published at the filing or priority date of the present application.

According to the distinctive characteristic of the invention, the body 1, made of biocompatible material, consists of surface receptacles 12 containing slow prolonged release substances selected from the classes of anti-inflammatory, anti-infection and bone regrowth promoter drugs. These substances are inserted into the receptacles 12 in a semi-solid form, for example pasty, so as to fill them stably.

The surface receptacles 12 are in the form of gratings of grooves provided for at least on the side walls 4, 5 of the body 1. Due to the hollow shape of the body 1, the surface receptacles 12 are normally provided for both on the outer surfaces and on the inner surfaces of the side walls 4, 5. Furthermore, such receptacles 12 can also be formed on other parts of the body 1, and in particular are also formed on the nose 11.

The arrangement represented in the drawings with orthogonal intersections of the gratings of grooves which form the receptacles 12 is provided purely by way of example, given that different arrangements which allow to maximise the amount of drugs that can be applied to the body 1 can also be envisaged.

Typically the pharmacological substances can be the following:

Growth promoters: drugs also with multimodal action, combining chemotactic, mitogenic, morphogenic, metabolic or apoptotic factors. They include BMP (bone morphogenetic proteins), in particular BMP-2 and BMP-7; VEGFs (vascular endothelial growth factors), which have been studied to promote the growth of blood vessels for the vascularisation of the bone; fibroblast growth factors. The use of statins has also been shown to promote the expression of BMP-2 in mRNA in osteoblasts.

Anti-infection: primarily broad spectrum antibiotics such as gentamicin and vancomycin Usual anti-inflammatory agents.

These substances are then normally added to excipients of various conventional types suitable to facilitate both their stability inside the receptacles 12 and the slow release thereof.

Obviously, the construction details and the embodiments may widely vary with respect to what has been described and illustrated, without departing from the scope of protection of the invention as described in the claims that follow.

The invention claimed is:

1. An intersomatic cage for vertebral stabilization, comprising:
    a generally prismatic hollow body having a protruding nose and configured to be inserted between two contiguous vertebrae so as to space them apart during a surgical insertion of the cage,
    wherein the generally prismatic hollow body includes upper and lower faces adapted to engage the two contiguous vertebrae, and opposed body side walls spaced laterally apart from each other and joining the upper and lower faces, the opposed body side walls each having inner and outer surfaces,
    wherein the inner and outer surfaces of the body side walls are formed with surface receptacles containing slow prolonged release substances selected from the classes of anti-inflammatory, anti-infection and bone regrowth promoter drugs,
    wherein the surface receptacles are in a form of gratings of grooves provided at least on the inner and outer surfaces of the body side walls, the gratings of groves forming orthogonal intersections with each other,
    wherein the surface receptacles in the form of gratings of grooves each include sidewalls and a bottom wall, and
    wherein the upper and lower faces include projections extending outwardly from outer surfaces thereof, and wherein the gratings of grooves are recessed inwardly from the inner and outer surfaces of the body side walls to the bottom wall.

2. The intersomatic cage according to claim 1, wherein said surface receptacles in the form of the gratings of grooves are provided on upper and lower surfaces of said nose and on a rear face of said body opposite the nose.

3. The intersomatic cage according to claim 1, wherein each of said side walls of the body includes a through hole.

* * * * *